United States Patent [19]
Albrektsson

[11] Patent Number: 4,728,332
[45] Date of Patent: Mar. 1, 1988

[54] ARTIFICIAL MENISCO-TIBIAL JOINT

[76] Inventor: Björn Albrektsson, Rödhakevägen 1, S-430 41 Kullavik, Sweden

[21] Appl. No.: 801,706

[22] Filed: Nov. 26, 1985

[30] Foreign Application Priority Data

Nov. 28, 1984 [SE] Sweden .................. 8405990

[51] Int. Cl.$^4$ .............................................. A61F 2/38
[52] U.S. Cl. ...................................................... 623/20
[58] Field of Search .................. 623/16, 18, 20, 21, 623/40, 41, 42, 43, 44, 45, 46

[56] References Cited

U.S. PATENT DOCUMENTS

| | | | |
|---|---|---|---|
| 4,085,466 | 8/1978 | Goodfellow et al. | 623/20 |
| 4,309,778 | 1/1982 | Buechel et al. | 623/20 |
| 4,353,136 | 10/1982 | Polyzoides et al. | 623/20 |
| 4,586,933 | 5/1986 | Shoji et al. | 623/20 |

Primary Examiner—Richard J. Apley
Assistant Examiner—David J. Isabella
Attorney, Agent, or Firm—Pollock, Vande Sande & Priddy

[57] ABSTRACT

An artificial menisco-tibial joint for a knee joint prosthesis of the kind which includes at least one tibial component on which the meniscus is movably disposed. The meniscus has a largely flat sliding surface against the tibial condyle which is provided with steering means imparting to the meniscus an ability to move in all directions along the tibial condyle. The steering means are so disposed that they limit the magnitude of the movement. The steering means consist preferably of two locating pins situated at a distance from each other which interact each with its own running track in the tibial condyle so that the meniscus, apart from a movement largely forwards and rearwards along the tibial condyle, is also imparted a sideways movement. Alternatively, the steering means consist of a posterior edge on the metal socket attached to the tibia.

4 Claims, 8 Drawing Figures

ARTIFICIAL MENISCO-TIBIAL JOINT

BACKGROUND OF THE INVENTION

The present invention relates to an artificial mensicotibial joint for a knee joint prosthesis of the kind which includes at least one tibial component on which the meniscus is movably disposed.

Different ways of dealing with knee joint destruction and other joint diseases or malformations in the knee joint through prosthetic surgical intervention are already known in the art. Disease-caused defects which may be concerned are rheumatic knee joint diseases and wear injuries which affect in the first instance joint cartilage and in the second instance underlying bone tissue which is worn away so that a varying degree of joint defect occurs.

The normal knee joint is based on a three-component relationship which permits both freedom of movement and firmness as well as a large contact area whereby concentration of stress is avoided. The two main components in the knee joint are the femur (thigh bone) and tibia (shin bone), the articulatory surfaces of which are connected to each other through a ligamentary apparatus in the form of ligaments and cruciate ligaments. The third component, the meniscus, is localized between the articulatory surfaces of the femur and tibia and functions as a movable shock-absorber. The meniscus accompanies the femur during rotation and the tibia in bending and stretching. The joint between the meniscus and femur may be designated as constrained, which means that there is good congruence between the articulatory surface of the femur and that of the meniscus (jont ball-joint socket relationship). The joint between the meniscus and tibia, in contrast, on account of the mobility of the meniscus and its relation to the tibia, is designated as non-constrained, permitting the tri-axial mobility which is necessary for, among other things, normal walking.

Several different types of prosthesis are already known in the art, both types of prosthesis which comprise only a femoral and tibial component and types of prosthesis which also include a third component which may be either fixed or movable (meniscus). With regard to different types of prosthesis and the requirements imposed on these as regards stability, resistance to mechanical wear, flexibility, etc., reference should be made to our parallel patent application Ser. No. 801,705.

There are principally two lines of designs of mobile tibial bearing elements available today, the non-constrained Oxford type as discussed in U.S. Pat. No. 4,085,466 to Goodfellow et al and the constrained New Jersey type of artificial meniscus as described in U.S. Pat. No. 4,309,778 to Buechel et al. The Oxford prosthesis, which is intended for cement fixation and consists of separate components for each joint chamber. It comprises an anatomically cupped femoral condylar prosthesis of metal and a metal tibial prosthesis, the upper surface of which is flat and articulates against the flat, lower surface of the "meniscus". This is a polyethylene disk located between the femur and the tibia. The upper surface of the meniscus facing towards the articulatory surface of the femoral prosthesis is cupped so that it fits well against the convexity of the femoral prosthesis. This contact may be said to be constrained. At the same time, the joint between the tibia and the lower surface of the meniscus is non-constrained, which means that the meniscus is self-locating with respect to the tibia. This combination of a constrained and a non-constrained joint affords the advantages of both these designs, a high degree of congruence and freedom for sliding movements in the horizontal plane.

In the Oxford prosthesis the menisco-tibial joint is stabilized only by the surrounding joint capsule and ligaments. In several cases, the meniscus has been reported to dislocate. For the most part it has then been squeezed posteriorly during knee flexion, probably because there are separate pivot points for the medial collateral ligament and the spherical femoral prosthetic surface respectively.

The femoral articulatory surface of the New Jersey prosthesis has a non-spherical femoral surface which offers less contact area towards the meniscus than that of the Oxford knee. The menisco-tibial joint is constrained by a steering strip along the lower surface of the meniscus, running in a curved dovetailed track in the tibial prosthesis. The track emerges towards the front and rear against the capsule enclosure giving sufficient firmness to prevent the meniscus from moving out of the joint. Since the track runs forwards and rearwards and describes a portion of the periphery in a circle with its center towards the center of the knee joint, the artificial meniscus will permit a certain rotation between the femoral and tibial prosthesis both of which are of metal and are intended for cement-free fixation in accordance with the porous coating principle. The knee prosthesis of Polyzoides et al (the gliding meniscus knee—Zimmer) is with respect to the meniscus more or less identical to the New Jersey knee.

The pros of the reduced risk of dislocation have to be weighed against the cons of the constraint. The New Jersey knee design seems to be very sensitive to surgical malalignment due to the complexity of the kinematics of the prosthesis. Disturbance of the delicate synchronization between, on the one hand, the tension of the ligaments and, on the other the three-dimensional arrangement of the four articulating femuro-tibial joint surfaces, could easily lead to reduction and even locking of menisco-tibial movements. Then the whole idea of the meniscus collapses. This is also the case if the components of the prosthesis are perfectly well aligned but fibrous tissue grows into the track and reduces the movements of the meniscus: This risk is obvious. Moreover, the slideways of the medial and the lateral meniscus do not have the same pivot point, which means that the meniscuses are likely to lock each other in certain positions where the bearing surfaces are not in harmony with the cruciates. Nor does the design make allowance for a relationship which applies to the natural knee, namely that the scope of movement of the meniscus in relation to the tibia is greater on the lateral side than on the medial side, which presumably contributes to inward rotation of the femur on the tibia at the final stage of knee extension. This rotational movement is believed to benefit stabilization of the knee via the so-called screw-home mechanism.

SUMMARY OF THE INVENTION

The above-mentioned disadvantages of the artificial meniscus included both the Oxford prosthesis and the New Jersey prosthesis have motivated us to develop a less constrained artificial meniscus. It differs from those two designs primarily by provision of a steering mechanism between the meniscus and tibia which both secures retention of the meniscus and permits anatomical kinematics. The underside of the meniscus is thus provided in one embodiment of the present invention, with two locating pins each of which runs in a preferably elliptical runway in a metal socket attached to the tibia. This groove permits all types of shearing movements, even lateral movements, thereby allowing for a certain compensation for surgical "malalignment". If, then, the femoral condyle is malplaced within certain limits laterally the meniscus can accompany it so that the femoral process actually sinks down into the socket of the meniscus. Moreover, the elliptical running groove is closed against the joint capsule and entirely covered by the meniscus, which significantly prevents ingrowth of tissue in the cavity.

An alternative embodiment of the invention prevents dislocation in the menisco-tibial joint by a posterior edge on the metal socket attached to the tibia. In this embodiment, the opposed articular surfaces of the menisco-tibular joint are flat without pins or runways.

Another embodiment of the invention is to imitate nature in such a way that the lateral meniscus is imparted greater freedom of movement in that its running track is larger than that for the medial meniscus. This thought will be carried to its extreme, so that the meniscus design is confined to the medial compartment, permitting the lateral femoral condyle to move freely against a fixed, completely flat tibial articulatory surface. Such a solution implies that the degree of freedom for sliding movements increases significantly in the lateral compartment but at the cost of increased stress concentration due to incongruity. Congruence is, however, not at all as essential in the lateral compartment as in the medial. The former is not subjected at all to the same compression forces as the medial, which takes up about 70% of of the compressive load.

The artificial menisco-tibial joint is characterized primarily in that the meniscus has a largely flat sliding surface towards the tibial condyle which is provided with steering means which impart to the meniscus an ability to move in all directions along the tibial condyle but which steering means are also so disposed that they limit the magnitude of the movement.

In one preferred embodiment of the present invention the steering means includes two locating pins which interact each with its own running groove in the tibial condyle. In one alternative embodiment of the invention the metal socket attached to the tibia has a posterior edge instead of running grooves, the edge being a hindrance against posterior overhang of the meniscus.

The invention will now be more closely described with reference to the accompanying drawings which show a suitable embodiment, wherein

DESCRIPTION OF THE PREFERRED EMBODIMENTS

Figure 1:
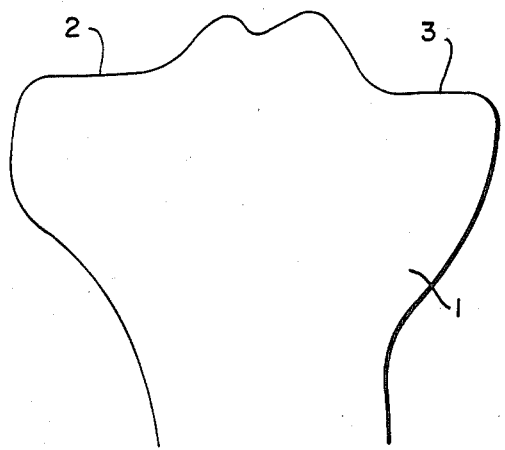
FIG. 1 shows the shin bone end (tibia) from the front before provision of a prosthesis.

Illustrated in FIG. 1 is the shin bone end (tibia) 1 of a knee joint viewed from the front. The articulatory surfaces 2, 3 of the tibia have a disease-caused defect which requires an articulatory replacement prosthesis which is to interact with a corresponding femoral component (not shown) in an artificial joint ball-joint socket relation. To provide room for the prosthesis the disease-caused defect to be found in connection with a joint-destructive disease or wear injury usually has to be expanded in conjunction with the prosthetic surgery so that healthy bone tissue is also removed. FIG. 1 shows the end contour of the tibia which has been removed both medially and laterally in order to create two largely horizontal planes for the articulatory surface replacement of the tibia. In this case, it is thus a matter of a joint replacement prosthesis which replaces a defective articulatory surface laterally and medially, whereas the central portion of the tibia remains unaffected.

The tibial prosthesis consists in principle of two segmental sockets 4, 5 which are firmly anchored in the bone tissue of the tibia in a manner already known in the art. How this anchorage is carried out is therefore not part of this invention and will not be described. The sockets are made of metal, for example commercially pure titanium with an upper smooth-ground surface which is treated to provide optimal resistance to mechanical wear. The smooth-ground surface of the metal socket forms a sliding surface for a movable meniscus 6 medially. As evident from FIG. 3, the outer contours of the sockets agree largely with the contour of the removed articulatory surface plane of the tibia. The shape of the meniscus 6 also agrees fairly well with this contour, but the meniscus is slightly smaller to permit a movement across the tibial socket in its lengthwise direction in a somewhat curved path and also in the lateral direction. The upper surface of the socket is provided with two running grooves or tracks 7 for steering of the meniscus. The running tracks are oblong, preferably elliptical, and their longitudinal axes form an angle with each other so that the path of movement of the meniscus will be curved, i.e. so that it largely describes a portion of the periphery of a circle with the center towards the center of the knee joint.

Figure 3:
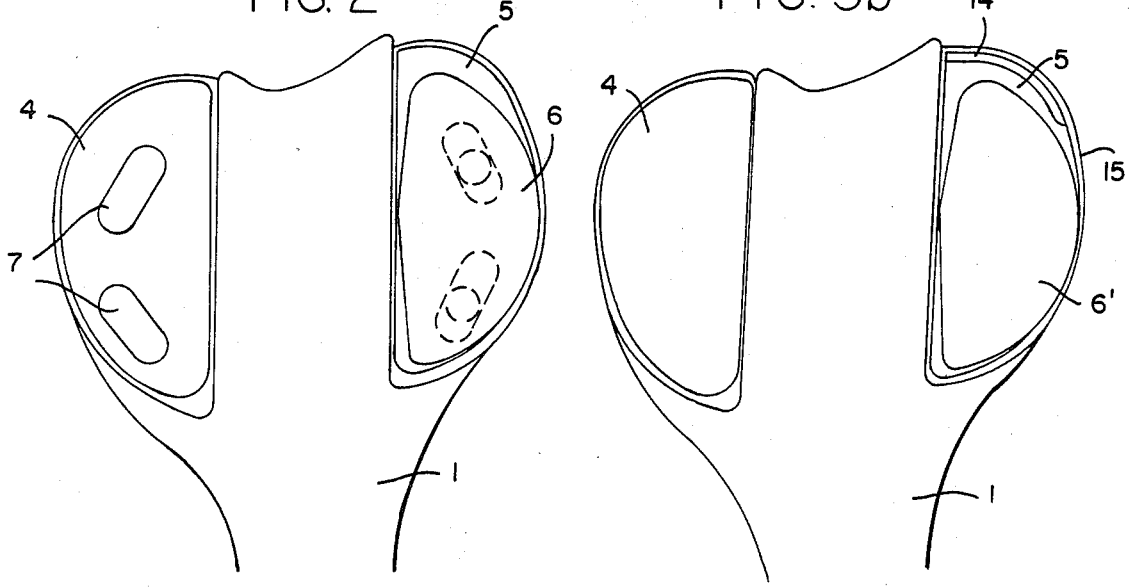
FIG. 3 shows the shin bone end (tibia) seen from the articulatory surface with an artificial, movable meniscus disposed on one tibial condyle.

As evident from FIG. 3 the running space formed by the running track and the sliding surface of the meniscus is completely closed to prevent ingrowth of tissue in the running space.

In FIG. 3 it is envisaged that an artificial meniscus shall be included both medially and laterally. The meniscus, however, is shown only on one tibial condyle. In the case that a meniscus is provided only medially (compare the above) the running tracks 7 in the socket 4 are missing and its articulatory surface is then completely flat.

Figure 4A:
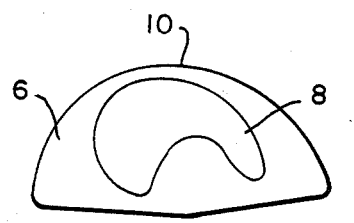
FIG. 4 shows the meniscus from above (FIG. 4a), from below (FIG. 4b) and from the side (FIG. 4c)
Figure 4B:
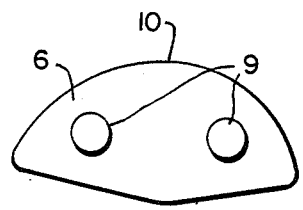
Figure 2:
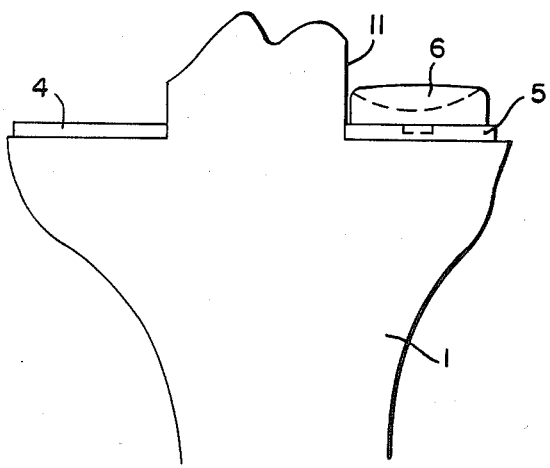
FIG. 2 illustrates the same view as FIG. 1 but after surgical removal and provision of a prosthesis.
Figure 4C:
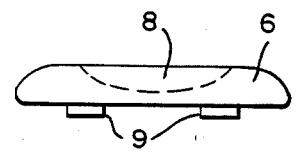

Shown in FIG. 4 is the artificial meniscus in three different views, from above in FIG. 4a, from below in FIG. 4b, and from the side in FIG. 4c. In our example, the articulatory surface 8 of the artificial mensicus against the femoral component is made congruent with the articulatory surface of the femoral component so that the stress concentration is reduced. It is on account of the motional geometry of the knee joint that the meniscus must be movably disposed on the tibia. The motional geometry of the meniscus is attained in that the flat lower surface of the meniscus, the sliding surface, is provided with two locating pins 9 which run in the two running tracks 7 in the socket. The locating pins are preferably cylindrical and with a diameter that enables the meniscus to move laterally up to about 3 mm and longitudinally in a slightly curved path of the magnitude of 5–12 mm. The length of the locating pins is such that they do not home in the running track 7.

The meniscus consists of a segment-shaped, virtually semi-circular body of polyethylene. It is thus limited by a curved line 10 adapted to the outer contour of the tibia and a straighter portion which borders against the vertical removal surface 11 of the central portion of the tibia. This straighter portion of the meniscus consists of two straight portions 12, 13 which are slightly angled in relation to each other to enable the meniscus to move in its curved path without bumping against the surface 11 of the tibia.

Figure 5B:
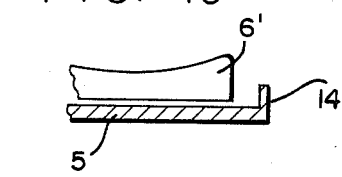
FIG. 5 shows the shin bone end (tibia) as in FIG. 3 but with the alternative embodiment of the invention in which the steering means comprises a posterior edge on the tibial socket.
Figure 5A:
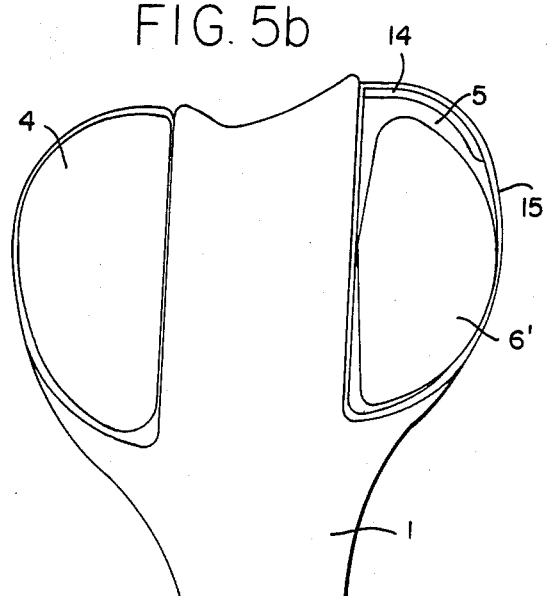

FIG. 5a illustrates the alternative embodiment of the mensico-tibial joint with an artificial meniscus shown on on tibial condyle. In this case there is a posterior edge 14 on the metal socket 5 attached to the tibia instead of running grooves or tracks, this edge being a hindrance against posterior overhang of the meniscus 6'. This means that in this embodiment the opposed articular surfaces of the menisco-tibial joint are flat without pins or runways.

The posterior edge 14 may occupy the entire curved line 15 of the socket but preferably only a part thereof in order to limit the magnitude of the backward movement of the mensiscus.

FIG. 5b is a partial cross-section of the socket 5 with the posterior edge 14 illustrating how the meniscus is prevented from dislocation.

I claim:

1. In an artificial menisco-tibial joint for a knee joint prosthesis of the kind which includes at least one tibial component on which the meniscus is movably disposed and wherein the meniscus has a largely flat sliding surface against the tibial condyle the improvement comprising:
   a steering means including two locating pins spaced a predetermined distance from each other and protruding from said sliding surface; and,
   said tibial condyle having at least one cavity forming a running track therein, said cavity being completely enclosed and wherein said running track defines substantially two longitudinal axes therethrough subtending an angle therebetween and said locating pins are disposed in each of said running track allowing longitudinal movement of the meniscus in a slightly curved path along said condyle as determined by said angle of the axes and spacing of said pins.

2. A menisco-tibial joint according to claim 1 wherein said locating pins are cylindrical and have a diameter that is slightly smaller than the width of the running track whereby said limited sideways movement of said meniscus is permitted in addition to said longitudinal movement.

3. A menisco-tibial joint according to claim 2 wherein the diameter of the locating pins is such that the meniscus can move sideways up to about 3 mm and longitudinally in a slightly curved path to about 5–12 mm.

4. A menisco-tibial joint according to claim 1, wherein the degree of freedom of the sliding movement of the meniscus is adjustable between greater degree provided by placement of the meniscus laterally in the knee joint and smaller degree by placement of the meniscus medially in the knee joint.

* * * * *